United States Patent [19]

Soszka et al.

[11] Patent Number: 5,171,634

[45] Date of Patent: Dec. 15, 1992

[54] PROCESS AND APPARATUS FOR PRODUCING COATED GLASS YARNS AND SIZING COATING THEREFOR

[75] Inventors: Barbara Soszka; Jacques Mahler; Eric Augier, all of Chambery, France

[73] Assignee: Vetrotex Saint-Gobain, Aubervilliers, France

[21] Appl. No.: 710,495

[22] Filed: Jun. 5, 1991

Related U.S. Application Data

[62] Division of Ser. No. 313,347, Feb. 17, 1989, Pat. No. 5,049,407.

[30] Foreign Application Priority Data

Feb. 12, 1986 [FR] France ................ 86 01917

[51] Int. Cl.$^5$ .................... D02G 3/18; D02G 3/36
[52] U.S. Cl. .................... 428/376; 57/249; 57/258; 428/378; 428/392; 428/442
[58] Field of Search ............ 427/53.1, 54.1, 55; 57/249, 258; 428/376, 378, 392

[56] References Cited

U.S. PATENT DOCUMENTS

| | | | |
|---|---|---|---|
| 2,723,215 | 11/1955 | Biefeld et al. | 154/91 |
| 3,425,862 | 2/1969 | Eakins | 117/126 |
| 3,853,605 | 12/1974 | Fahey | 427/178 |
| 4,263,337 | 4/1981 | Login | 427/54.1 |
| 4,537,610 | 8/1985 | Armstrong et al. | 65/3.44 |
| 4,636,405 | 1/1987 | Mensah et al. | 427/54.1 |
| 4,741,958 | 5/1988 | Bishop | 427/54.1 |
| 4,758,447 | 7/1988 | Broer et al. | 427/44 |
| 4,769,286 | 9/1988 | Le Noane | 427/54.1 |
| 4,770,898 | 9/1988 | Sugai et al. | 427/54.1 |

FOREIGN PATENT DOCUMENTS

| | | |
|---|---|---|
| 002006 | 5/1979 | European Pat. Off. |
| 2073472 | 10/1971 | France |
| 81-59646 | 5/1981 | Japan |
| 60-71549 | 4/1985 | Japan |
| 60-83908 | 5/1985 | Japan |

OTHER PUBLICATIONS

Kimura et al., "Coating Tech. for High Speed Drawing", Sixth European Conference on Optical Communication, York, England, Sep. 1980, pp. 57-60.

Paek et al., "High speed coating of optical fibers with UV curable materials at a rate of greater than 5M/sec", Applied Optics, vol. 20 #23, Dec. 1981, pp. 4028-4034.

Chemical Abstracts, vol. 95, No. 18, Nov. 2, 1981, p. 296, No. 155307r.

Chemical Abstracts, vol. 103, No. 12, Sep. 23, 1985, p. 261, No. 91936u.

Chemical Abstracts, vol. 103, No. 18, Nov. 1985, p. 270, No. 146197m.

Primary Examiner—James C. Cannon
Attorney, Agent, or Firm—Pennie & Edmonds

[57] ABSTRACT

A process for producing coated glass yarns which comprises drawing a plurality of fibers formed from strands of molten glass, applying to the strands a sizing coating comprising at least a monounsaturated or polyunsaturated oligomer and a photostarter composition such as a photoinitiator compound, a photosensitizer compound or a mixture thereof and optionally an organic solvent and an additive composition comprising at least one of a wetting agent, an adhesion promoting agent, an anti-shrinking agent and a coupling agent, gathering the coated strands into a yarn and irradiating the coated yarn with a source of actinic radiation. An apparatus for performing this process comprises a spinneret having a plurality of nozzles or orifices, from which strands of molten glass are discharged, means for drawing a plurality of glass fibers from the spinneret, at least one coating applicator for applying the sizing coating to the glass fibers, guide means for gathering the coated fibers into a yarn and an irradiation enclosure wherein the coating is crosslinked and/or polymerized by the effect of at least two sources of actinic, preferably ultraviolet, radiation.

15 Claims, 2 Drawing Sheets

PROCESS AND APPARATUS FOR PRODUCING COATED GLASS YARNS AND SIZING COATING THEREFOR

This is a divisional application of application Ser. No. 07/313,347, filed Feb. 17, 1989, now U.S. Pat. No. 5,049,407.

TECHNICAL FIELD

The invention relates to a process and an apparatus for producing coated glass yarns, comprised of a plurality of coated glass fibers, and finished products having improved mechanical, chemical and thermal properties.

BACKGROUND OF THE INVENTION

A number of techniques have been disclosed in the prior art for improving the properties, in particular the mechanical properties, of glass fibers. For example, U.S. Pat. No. 2,723,215 describes a process for protecting glass fibers from atmospheric moisture during the fiber-drawing operation which occurs directly after their formation. The technique involves the deposition of a sufficient amount i.e., in the range of 4-30% by weight or more, of a protective coating, to completely coat a yarn formed from these fibers. This protective coating is deposited in the liquid state and is thereafter solidified by cooling the coated material. The composition comprises a base of thermoplastic synthetic or natural waxes which may optionally include other natural or synthetic products of high molecular weight.

U.S. Pat. No. 4,537,610 discloses an alternate embodiment of the technique described above in that a thermoplastic coating is applied to the yarn in a zone located directly below the spinneret which forms the glass fibers. These coated yarns are, however, invariably crushed during their passage through the cutting machine. They must then be reheated up to the softening temperature of the coating composition to enable them to resume their initial shape.

Although the process described in U.S. Pat. No. 2,723,215 is effective in improving the mechanical properties of the coated yarns obtained thereby, it has been found to have a detrimental effect on the thermal and chemical properties of the yarn. In fact, after undergoing the coating process described by the '215 patent, the yarn produced thereby suffers from increased heat sensitivity and has a relatively low thermal stability.

SUMMARY OF THE INVENTION

Applicants have discovered a novel method and apparatus for forming coated glass yarns having improved mechanical, thermal and chemical properties.

A first embodiment of this invention comprises a process for producing such yarns which includes the steps of mechanically drawing a plurality of fibers formed from strands of molten glass flowing through hollow stud means connecting with a plurality of nozzles orifices located in the bottom of a spinneret. A coating layer of a sizing composition either emulsion or solution aqueous or not is then applied to the surface of the glass fibers. This coating contains a) at least a monounsaturated or polyunsaturated oligomer such as polyester acrylates, modified cellulose or starch, epoxy acrylates, silicone compounds and urethane acrylates and optionally further including chlorine as an activator element; b) at least a monounsaturated or polyunsaturated monomer, preferably an acrylic monomer; c) optionally an organic solvent; d) a photostarter composition comprising either: 1) a photoinitiator compound such as benzoin, acetophenone, sulfonylacetophenone and their respective derivatives or, 2) a photosensitizer compound selected from among the thioxanthones, benzophenone and the benzophenone derivatives, or 3) a mixture of both a photoinitiator and a photosensitizer compound; and e) an additive composition which may optionally include at least one of a wetting agent such as diethyl polyacrylate, an adhesion promoting agent such as a methacrylic derivative or a silane compound, an antishrinking agent such as a chlorinated oligomer or spiro compounds such as spiro orthocarbonate, spiro orthoester and a coupling agent such as a silane compound. At least one component of the sizing composition may optionally be applied separately from the remaining constituents thereof.

Following the above-described coating step, the individual glass fibers are gathered together into a yarn which is thereafter irradiated with actinic radiation, preferably ultraviolet radiation, so as to crosslink and/or polymerize the fiber coating. The irradiation step is preferably carried out in an oxygen-free environment and optionally, the coated yarn may thereafter be further subjected to additional coating/irradiation treatments utilizing the same or different finish compositions so as to obtain coated fibers having useful properties for various applications.

In an alternate embodiment of the method described above, the spinneret may be provided with a source of a dry inert gas such as dry nitrogen, for blowing through the fibers as they are produced. The inert gas thereafter forms a protective envelope around the glass fibers as they are produced and moves with them at least to the coating zone. The presence of this protective gaseous envelope prevents the fibers from becoming exposed to moisture in the atmosphere prior to the coating operation, which may detrimentally affect the resultant product.

A further embodiment of the invention comprises an apparatus for producing coated yarn of the type described above. The apparatus comprises a receptacle for containing and/or supplying a sufficient amount of molten glass and having a plurality of orifices through a bottom portion thereof. Each of these, nozzles or orifices is in communication with a hollow stud means from which molten glass is discharged. Mechanical drawing means are provided to draw a plurality of continuous fibers of molten glass from the spinneret.

At least one coating application means is provided, such as a roller applicator, wherein a bottom portion of said roller is bathed in a bath of the sizing composition. The roller is optionally connected calibrating blade to facilitate the formation of a uniform layer of the sizing composition on the roller. In alternate embodiments of the invention, the coating application means may be spray means or other means. The applicator means of the invention is used to deposit a coating of the sizing composition on the fibers as they are drawn over the roller. Following this coating operation, the fibers are gathered into a yarn and then irradiated with a predetermined amount of an actinic radiation.

The means for irradiating the coated yarn of the invention comprises: a ventilated enclosure having at least one radiation emitting tubes mounted therein, said tubes being specifically selected for their particular emission spectrum and having a semi-elliptical reflector member positioned behind them. Each of the radiation emitting tubes is mounted in the enclosure on moveable rod means, said means being capable of adjusting the distance between the tube and the yarn. Further, a silica tube may be placed vertically in the axis of the enclosure along its entire height and positioned to protect the radiation emitting tubes from accidental contamination by the finish composition. The effect of the actinic radiation, which is preferably in the ultraviolet range, is to crosslink and/or polymerize the sizing coating.

Once the coated yarn has been treated as indicated above, it may be received for storage on rotating spindle means. Optionally, a cutting apparatus may also be provided for dividing the yarn into useful lengths.

In a further embodiment, the radiation enclosure may be provided with conduit means for delivering a current of a dry inert gas such as dry nitrogen to surround the coated yarn as it passes there with a dry, inert atmosphere to prevent any interference due to the presence of atmospheric moisture. Further, the zone directly below the spinneret may also be provided with means for directing a flow of inert gas through the fibers as they are produced. This gas forms an envelope around each fiber and travels with each fiber into at least the coating enclosure so as to further protect the fiber from the effect of atmospheric moisture.

DETAILED DESCRIPTION OF THE PREFERRED EMBODIMENTS

Figure 1:
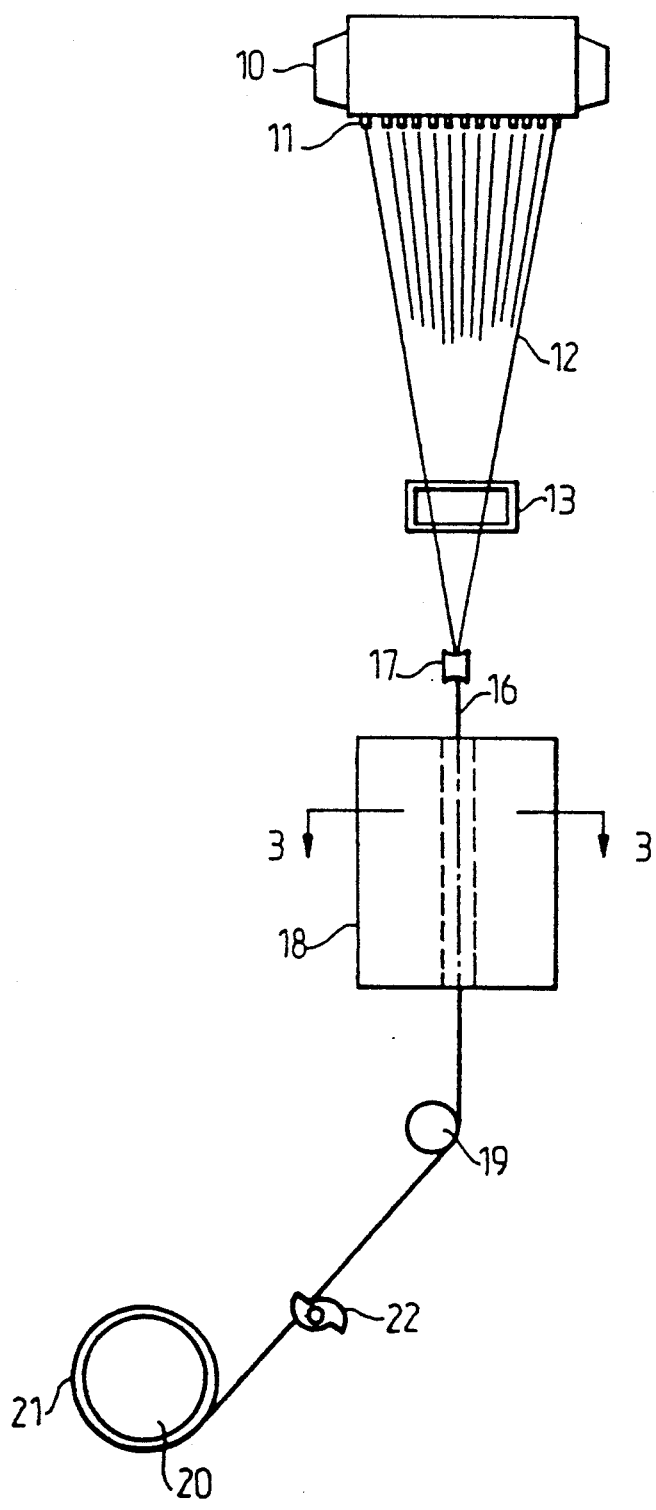
FIG. 1 is a front schematic view of the apparatus of the invention.

The process of the present invention has, as its object, the improvement of the mechanical, thermal and chemical properties of a yarn formed of a plurality of glass fibers which are produced by the mechanical drawing technique. A further object of the invention is the formation of a yarn whose characteristics, such as its rigidity and its integrity, may be varied so as to render it useful for numerous applications.

The process of the invention comprises mechanically drawing a plurality of glass fibers from strands of molten glass produced by a spinneret apparatus. The fibers may then be coated with a sizing deposited in the form of a solution or an emulsion optionally in water. This sizing preferably comprises a monounsaturated or polyunsaturated oligomer and a photostarter composition. An optional organic solvent may be added to the mixture as well as a monounsaturated or polyunsaturated monomer, such as an acrylic monomer. Once the separate strands have been coated, they are gathered together into a yarn and the yarn is then subjected to actinic radiation.

By use of the term "photostarter", applicants mean to include both photoinitiator compounds, i.e., molecules which when exposed to a specific wavelength of energy form reactive species which start the chain reaction to cause polymer formation, and photosensitizers, i.e., compounds which will transfer energy an and form free radicals by interacting with another chemical compound. Further, by the term "actinic radiation", applicants mean to include all types of radiation which are able to induce chemical reaction, including ultra-violet and laser radiation.

A first consideration with regard to applicants' process is the drawing speed of the glass fibers, which may reach several tens of meters per second. At such speeds the duration of exposure and the amount of coating material deposited upon the glass fibers is critical. Another important feature of the invention is the relatively small distance which separates the bottom of the spinneret from the device for drawing the yarn, i.e., generally less than 5 meters. Due to this limited separation between the components of applicants, apparatus, the glass fibers must be coated, gathered into a yarn and the coating must then be polymerized and/or crosslinked in less than one second.

With regard, therefore, to the coating composition chosen for use in applicants, process as described herein, the choice of oligomers for use in the sizing is made as a function of the final properties which are required of the polymer obtained after irradiation of the yarn, as well as the speed of polymerization which can be obtained with these compounds. Preferred examples of these oligomers include polyester acrylates, modified celluloses and starches, epoxy acrylates, silicon compounds and urethane acrylates. These oligomers may also include activator elements, such as chlorine. The oligomers may be chosen so as to obtain finishes whose viscosity is below pre-set limits. In order to prepare such compositions, the oligomers must be chosen from those whose molecular weight is preferably between about 500 and 5,000.

The other required component of the coating sizing is the photostarter material. Within the context of the invention, the sizing may comprise either a photoinitiator, a photosensitizer or a mixture of the two. When the drawing speed of the fibers is high and/or when a high degree of polymerization is desired, it is preferable to include a photoinitiator in the composition. Further, when the sizing contains both a photoinitiator and a photosensitizer, it is preferable to use more of the former than the latter. When the drawing speed is greater than or equal to 15 meters/second, the finish must contain a photoinitiator and optionally a photosensitizer. The total amount of photostarter material to be utilized in the composition must be greater than or equal to 10% by weight, the percentage being calculated with relation to the total weight of oligomer and, if applicable, of the monomer included therewith. When the sizing contains one or more photosensitizers with no photoinitiators, it is necessary to add a hydrogen donor, such as an amine.

The preferred photoinitiators utilized in applicants' sizing coating composition preferably include benzoin, acetophenone or sulfonylacetophenone and their respective derivatives. Further, applicants' preferred photosensitizer compositions include benzophenone and its derivatives and the thioxanthones. The viscosity of the resultant finish may optionally be adjusted by the addition of an organic solvent, the nature and amount of this solvent being dependant upon the oligomer(s) utilized in the coating composition. In addition, the solvent selected for use in applicants' process must be capable of complete elimination during the irradiation of the yarn and it must therefore not have too high a boiling temperature. Since the device for coating the fibers is located near the bottom of the spinneret, which is heated by the Joule effect, the solvent which is selected should not exhibit a low flash point and/or ignition point in order to avoid the hazards of fire and explosion.

As described above, applicants' coating sizing may also contain one or more monounsaturated or polyunsaturated monomers which may optionally be carried in an organic solvent. These additional monomers have an effect similar to that of the solvent in that they act as a diluent and thus make it possible to adjust the viscosity of the sizing. These reactive diluents, however, do participate in the polymerization reaction and, like the oligomers, they are selected with a view toward the properties desired for the final polymer. The sizing may also comprise one or more additives selected wetting agents, adhesion promoters, antishrinking agents and coupling agents.

The main function of a wetting agent is to promote the penetration of the sizing between the glass fibers and to assure the homogeneity of its distribution within the yarn. A preferred example of this material is diethyl polyacrylate. The function of the adhesion promoter, preferably selected from among the methacrylic derivatives and silane compounds, is to ensure the fixing of the finish to the surface of the glass fibers. The antishrinking agent may be added to prevent the surface of the glass fibers from becoming locally uncovered and the sizing from becoming detached. This material is preferably a chlorinated oligomer, a spiro orthoester or a bicyclo orthoester. Finally, the coupling agent, which facilitates the chemical bonding between the sizing and the surface of the fiber, is preferably a silane compound Preferred relative amounts of the sizing coating compositions of the invention include the following:
- oligomers: 0 to 100, preferably 50 to 80, weight percent
- monomers: 0 to 100, preferably 17 to 28, weight percent
- photoinitiators: 2 to 20, preferably 4 to 11, weight percent
- photosensitizers: 0 to 18, preferably 2 to 10, weight percent
- solvents: 0 to 35, preferably 10 to 20, weight percent
- coupling agent: 0.1 to 5, preferably 0.3 to 2.5 weight percent
- wetting agent: 0.05 to 2, preferably 0.1 to 0.5 weight percent
- adhesion promotive agent: 0 to 2 weight percent
- antishrinking agent: 0 to 2 weight percent Also, the amount of sizing coating deposited on the yarn (in weight percent based on the weight of the glass) ranges from 5 to 80 percent, whereas the amount of polymerized or crosslinked material in the sizing coating ranges from about 5 to 100 percent by weight, thus providing a yarn having ultimate tensile strengths between about 75 and 96 g/tex.

In order to produce a yarn having the greatest possible tensile strength, therefore, a sufficient amount of the sizing coating to prevent the passage of water vapor in atmosphere must be deposited upon the surface of the glass fibers immediately subsequent to their formation. These fibers are then gathered into a yarn wherein each fiber, as well as the yarn itself, is sheathed by this protective coating.

A process for enhancing the coating effect and thus further preventing the contamination of these newly formed glass fibers with water vapor from the atmosphere is to direct a flow of a dry, preferably inert gas, i.e., nitrogen, through the fibers produced at the bottom of the spinneret which, due to an entrainment effect caused by the high drawing speed of these fibers, encompasses the entire outer surface of each fiber and follows the fibers in their movement, at least up until the moment when they are coated with the sizing. It has therefore been determined that the degree of polymerization undergone by the sizing is greater when the fibers are first entrained in a dry gas, all other conditions being otherwise equal.

It is also possible to increase the polymerization of the sizing by maintaining the yarn in an oxygen-free atmosphere, at least while it is undergoing irradiation. The degree of polymerization may also be dependent on other factors, such as the number and size of the fibers which constitute the yarn and/or the wavelength of the radiation used to irradiate it.

When such a yarn is made from a large number of fibers and/or fibers having a thick diameter, the effect of the radiation on the sizing located on the surface of the glass fibers located at the core of the yarn is negligible. When this occurs, the degree of polymerization of the sizing is not identical throughout the entire mass of the yarn, i.e., the sizing at the core of the yarn is only slightly polymerized while the sizing on the outer surface of the yarn is totally polymerized. This variance in the polymerization of the sizing generally does not produce satisfactory yarns since discontinuities may occur within the insufficiently polymerized sizing.

In certain applications, however, this heterogeneous polymerization may constitute a considerable asset. For example, yarns of this type may be utilized as a glueless winding between other yarns wherein the sizing located at the core thereof will later be subjected to further polymerization by the addition of, for example, thermal energy. The drawbacks associated with this technique may also be overcome by increasing the intensity of the radiation. This technique is not entirely satisfactory, however, because the irradiation devices which are normally used for this purpose emit a radiation having a wavelength spectrum which is not suited to the absorption ranges of the various substances constituting the sizing of the yarn and/or to the composition of the fiber itself.

Alternatively, excessive irradiation of the yarn may lead to an opposite effect from that which is desired by, for example, promoting excessive polymerization on the outside of the yarn. The most effective method has been determined to involve the combination of two radiation sources whose wavelengths are selected as a function of the absorption spectra of the glass and of the constituents of the sizing.

The amount of sizing deposited upon the yarn is preferably greater than or equal to 5% of the yarn mass to be coated. In order to build up the sizing layer on the yarn surface and thus obtain yarns having particular properties, a thick coating may either be deposited in a single operation or, after subjecting a coated yarn to the action of an actinic radiation, the yarn may be coated one or more additional times, each coating application being subjected to an actinic radiation source prior to the next coating operation. This process may be repeated as many times as is necessary. The subsequent sizing layers may be comprised of the same material as that deposited in previous coating operations or they may optionally be different.

The properties of a yarn made up of a plurality of sizing-coated glass fibers, i.e., its rigidity, its integrity (the degree of bonding of the fibers to one another) and its solubility in organic solvents, such as styrene or toluene, depend on the degree to which the sizing is polymerized and the nature of its formulation. Use of the process described above therefore permits one to obtain yarns having variable chemical, mechanical and thermal properties.

Figure 2:
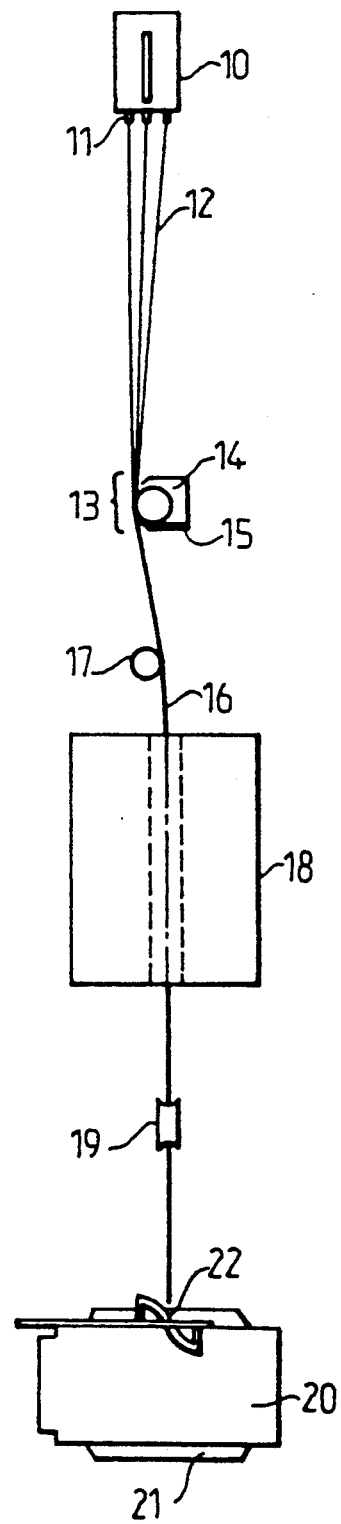
FIG. 2 is a side schematic view of the apparatus of FIG. 1.

With regard to the apparatus of the invention, FIGS. 1 and 2 illustrate schematic representations of the various aspects thereof. In order to facilitate an understanding of the method of operation of this apparatus, features of the device which appear in both FIGS. 1 and 2 have been labeled with the same identifying number.

The apparatus comprises a spinneret 10 generally constructed of a metal alloy and heated by the Joule effect, i.e., the effect due to the first law of thermodynamics regarding the incontrovertability of the various forms of energy. The spinneret is used either to maintain in a liquid state a supply of molten glass provided by a source such as a float bath (not shown) or to remelt glass originally supplied in the molten state but which has subsequently became solidified. The bottom of spinneret 10 is pierced with a number of orifices which may be extended by hollow studs 11 from which strands of molten glass are discharged. These strands are mechanically drawn and give rise to continuous glass fibers 12.

Fibers 12, which are initially arrayed in a fanned out arrangement, pass over coating device 13 which deposits a layer of the sizing coating thereupon. Coating device 13 is preferably a roller 14 whose lower portion is bathed in a supply of sizing bath 15. Roller 14 may optionally be associated with a calibrating blade (not shown) to form a uniform layer of the sizing on the surface of roller 14. This device is described in European Patent No. 0 002 006.

The sizing coating may, of course, be deposited by alternate means well known to those skilled in the art, such as spray techniques, working holes fed by a metering pump and foaming devices. It is also possible to separately deposit one or more constituents of the sizing composition on fibers 12. Thus, it is possible to deposit one sizing, such as a silane, on fibers 12 with coating device 13 followed by a second coating sizing with a second coating device, identical to first or not and placed below it.

The coated fibers which result from this operation are gathered into a yarn 16 by an element such as assembly wheel 17. Yarn 16 then passes through irradiation apparatus 18 wherein it is subjected to an actinic radiation. The yarn may, of course, be coated and irradiated more than once with the same or different materials by utilizing more than one such device for this purpose. At the outlet of apparatus 18, yarn 16 travels over guiding element 19, such as a small wheel, before being wound on a rotating spindle 20. Spindle 20 is driven by a motor fastened to a frame (not shown). Yarn 16 is thereafter directed into winding 21 by element 22.

The appearance of the yarn may vary as a function of the application for which it is intended. Thus, yarn 16 may be drawn directly through a cutting machine and transformed into cut yarn. It can also be drawn over a device which distributes it over the entire width of a conveyor belt so as to create a felt formed of continuous yarns.

Figure 4:
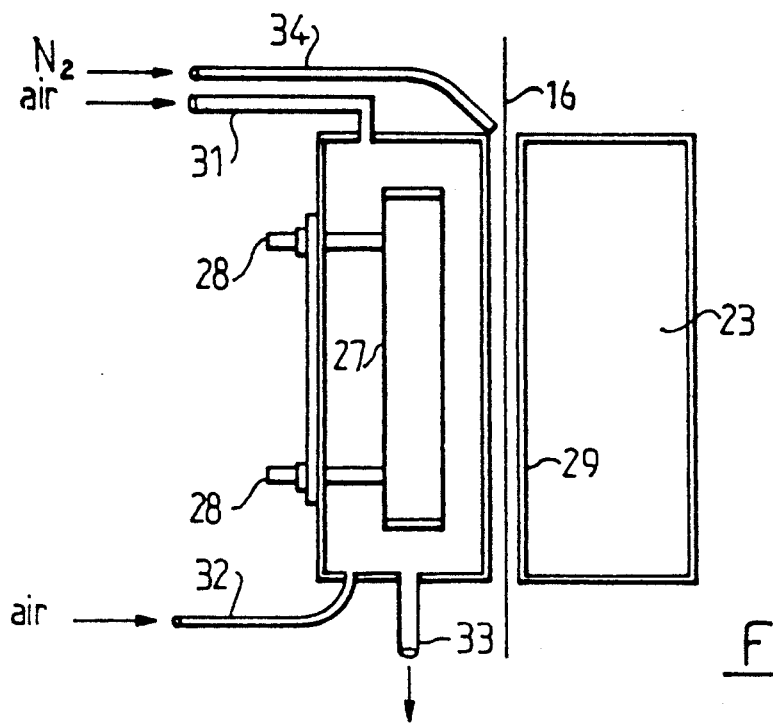
FIG. 4 is a sectional view taken along line 4—4 of FIG. 3.
Figure 3:
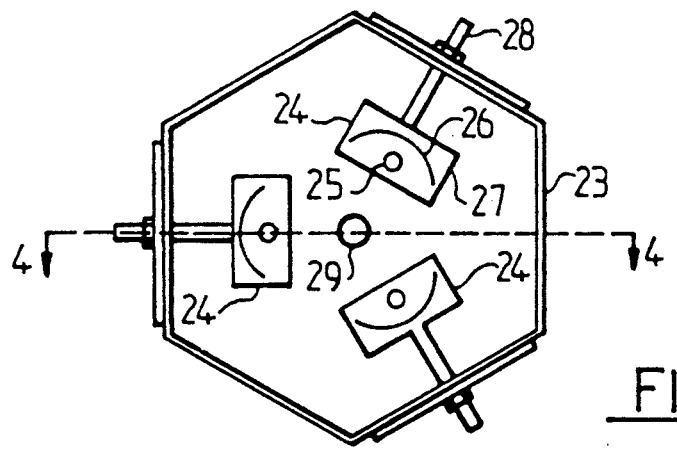
FIG. 3 is a sectional view taken along line 3—3 of FIG. 1.

FIGS. 3 and 4 illustrate the structure of the device used for irradiating yarn 16. The device is composed of a ventilated enclosure, several sources for emitting actinic radiation, i.e., preferably ultra-violet radiation and an electrical control device (not shown).

In the embodiment depicted in FIG. 3 the enclosure is bounded by hexagonal chamber 23 containing 3 radiation-emitting sources 24 placed 120° apart. Each radiation source 24 utilizes an emitting tube 25. Tube 25 can be excited at high, medium or low pressure through the use of electrodes or microwaves and it is specifically chosen for its particular emission spectrum. It may therefore be doped with rare gasses or metals depending upon the type of product which is sought.

A semi-elliptical reflector 26 is positioned directly behind tube 25. This unit is mounted on case 27 which is attached to the wall of chamber 23 by sliding rods 28 which make it possible to adjust the distance separating emitting tubes 25 from yarn 16. A silica tube 29 is placed vertically in the axis of chamber 23 along its entire height. The yarn 16, guided by elements 17 and 19, advances in the axis of tube 29. The purpose of tube 29 is to protect the emitters from being accidentally sprayed with the sizing coating. It is also possible to protect the emitters directly through the use of silica windows. In this case, tube 29 is no longer required.

Chamber 23 is further equipped with conduits 31 and 32 which facilitate the passage of compressed air used to ventilate the interior of the chamber. This air is then removed through pipe 33. An additional pipe 34, directed to the upper portion of tube 29, makes it possible to deliver a current of an inert gas such as nitrogen. This permits yarn 16 to be surrounded with an inert atmosphere within the irradiation zone. Additionally, rods 28 are preferably adjusted so that the focal points of the semielliptical reflectors 26 are merged in the path of yarn 16.

Figure 5:
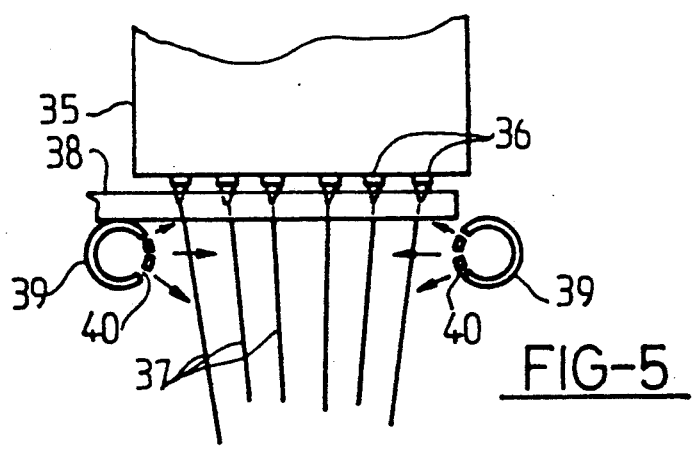
FIG. 5 is a partial front schematic view of the an alternate embodiment of applicants' apparatus.

Turning now to FIG. 5, the apparatus illustrated therein may be included in an alternate embodiment of the device schematically represented in FIGS. 1 and 2. FIG. 5 illustrates a lower portion of spinneret 35 equipped with studs 36 from which glass fibers 37 are drawn. The bottom of spinneret 35 is equipped with a series of cooling fins, 38, regularly installed between the rows of studs 36.

Immediately below fins 38, ducts 39 may be installed on either side of spinneret 35, parallel to the longest sides thereof. The wall of each of ducts 39 is pierced with one or more rows of orifices or slots directed toward the fiber drawing zone. During the fiber drawing operation, ducts 39 are supplied with a dry gas, preferably nitrogen, which is blown through orifices 40 in the direction of fibers 37, thus surrounding them as soon as they are formed. The fibers become entrained within the dry gas, which forms an envelope around them and accompanies them as they move. The use of this gas effectively prevents any contact between the surface of the fibers and the water in the atmosphere.

The following examples were performed upon an installation utilizing a device for irradiating yarn 16 similar to that described above. The amount of radiation delivered was variable, ranging generally between about 50–200 watts per linear centimeter of emitting tube 25. The wavelength of the radiation emitted was between 200 and 420 nanometers. The glass used was well known to those of ordinary skill in the art as "E" glass. The sizing was deposited in a single coating operation with the use of a calibrating blade roller, as previously described. The drawing speed adopted for the first seven examples was 15 meters/second.

EXAMPLES

The following examples illustrate the effect of various sizings on the rate of polymerization, all other conditions being substantially equal. These examples are disclosed for the purposes of illustration only and are not to be construed as limiting the scope of the invention in any manner.

EXAMPLE I

The composition of the sizing coating was:

| Oligomer: | 77.2%* | Polyester polyacrylate (marketed under the trade name Ebecryl 810 by Union Chimique Belge) |
|---|---|---|
| Photoinitiator: | 7.8% | benzyl dimethyl ketal |
| Solvent: | 15.0% | methyl ethyl ketone |
| L.O.I = 15.3% | | |
| (LOI = the amount of sizing coating deposited on the yarn, expressed in a percentage in relation to the weight of the glass) | | |
| TC = 42% | | |
| (TC = the amount of polymerized and/or crosslinked material in the sizing coating, expressed in percentage by weight in relation to the total amount of sizing coating.) | | |

*All values given are in weight percent.

EXAMPLE II

The composition of the sizing coating was:

| Oligomer: | 55.8% | epoxyacrylate (marketed under the trade name Ebecryl 600 by Union Chimique Belge) |
|---|---|---|
| Monomer: | 18.6% | hexanediol diacrylate |
| Photoinitiator: | 10.6% | benzyl dimethyl ketal |
| Solvent: | 15.0 | methyl ethyl ketone |
| LOI = 15.6% | TC = 100% | |

EXAMPLE III

The composition of the sizing coating was:

| Oligomer: | 74.4% | Polyester polyacrylate (marketed under the trade name Ebecryl 830 by Union Chimique Belge) |
|---|---|---|
| Photoinitiator: | 4.0% | hydroxyl-1-cyclohexyl phenyl ketone |
| Photosensitizer: | 6.6% | benzophenone |
| Solvent: | 15.0% | methyl ethyl ketone |
| LOI = 19.9% | TC = 75% | |

EXAMPLE IV

The composition of the sizing coating was:

| Oligomer: | 74.4% | polyester polyacrylate (Ebecryl 830) |
|---|---|---|
| Photoinitiator: | 5.3% | hydroxyl-1-cyclohexyl phenyl ketone |
| Photosensitizer: | 5.3% | benzophenone |
| Solvent: | 15.0% | methyl ethyl ketone |
| LOI = 32.8% | | Rigidity: high |
| TC = 85% | | Integrity: maximum |

EXAMPLE V

The composition of the sizing coating was:

| Oligomer: | 55.8% | epoxyacrylate (Ebecryl 600) |
|---|---|---|
| Monomer | 18.6% | hexanediol diacrylate |
| Photoinitiator: | 5.3% | hydroxy-1-cyclohexyl phenyl ketone |
| Photosensitizer: | 5.3% | benzophenone |
| Solvent: | 15.0% | methyl ethyl ketone |
| LOI = 11.1% | | Rigidity: high |
| TC = 43% | | Integrity: very good |
| Ultimate tensile strength = 82 g/tex | | |
| Solubility in toluene = 45% | | |

EXAMPLE VI

The composition of the sizing coating was:

| Oligomer: | 55.8% | epoxyacrylate (Ebecryl 600) |
|---|---|---|
| Monomer | 18.6% | hexanediol diacrylate |
| Photoinitiator: | 10.6% | 2-hydroxy-2-methyl-1-phenyl propane-1-one |
| Solvent: | 15.0% | methyl ethyl ketone |
| LOI = 11.1% | | Rigidity: high |
| TC = 46% | | Integrity: very good |
| Ultimate tensile strength = 88 g/tex | | |

EXAMPLE VII

The composition of the sizing coating was:

| Oligomer: | 55.8% | epoxyacrylate (Ebecryl 600) |
|---|---|---|
| Monomer | 18.6% | hexanediol diacrylate |
| Photoinitiator: | 10.6% | hydroxy-1-cyclohexyl phenyl ketone |
| Solvent: | 15.0% | methyl ethyl ketone |
| LOI = 16.4% | | |
| TC = 100% | | |

EXAMPLE VIII

This sizing was deposited upon fibers drawn at a speed of 20 meters/second. The composition of the sizing coating was:

| Oligomer: | 76.92% | polyester polyacrylate (Ebecryl 810) |
|---|---|---|
| Photoinitiator: | 5.38% | benzyl dimethyl ketal |
| Photosensitizer: | 2.31% | benzophenone |
| Bridging Agent: | 0.39% | methacryl silane |
| Solvent: | 15.00% | methyl ethyl ketone |
| LOI = 13% | | Ultimate tensile strength = 75 g/tex |
| TC = 13% | | Solubility in toluene = 51% |

EXAMPLE IX

This example illustrates the positive influence of a wetting agent on the rate of polymerization. The composition of the sizing was:

| Oligomer: | 77.27% | Polyester polyacrylate (Ebecryl 810) |
|---|---|---|
| Photoinitiator: | 7.73% | hydroxyl-1-cyclohexyl phenyl ketone |
| Solvent: | 15% | methyl ethyl ketone |
| LOI = 27% | ds = 15 | TC = 50% |
| | ds = drawing speed = 15 m/s | |
| Wetting agent: | 0.2% | diethyl polyacrylate (marketed under the trade name "Modaflow" by |

-continued

| | | Monsanto) |
|---|---|---|
| LOI = 29% | ds = 25 m/s | TC = 78% |
| LOI = 30% | ds = 30 m/s | TC = 79% |
| rigidity: very high | integrity: maximum | |
| ultimate tensile strength: 70 g/tex | | |

EXAMPLE X

| Oligomer: | 70% | polyester polyacrylate (Ebecryl 830) |
|---|---|---|
| Monomer: | 20% | trimethylol propane triacrylate |
| Photoinitiator: | 5% | hydroxy-1-cyclohexyl phenyl ketone |
| Photosensitizer: | 5% | benzophenone |
| LOI = 8.5% | ds = 23 | TC = 45% |
| LOI = 18.7% | ds = 19 | TC = 40% |

EXAMPLE XI

| Oligomer: | 62.2% | epoxyacrylate (Ebecryl 600) |
|---|---|---|
| Monomer: | 27.8% | hexanediol diacrylate |
| Photoinitiator: | 10% | hydroxy-1-cycolhexyl phenyl ketone |
| LOI = 23% | | TC = 90% |

EXAMPLE XII

The results of this test demonstrate the respective effects of the drawing speed and the concentration of photostarter on the polymerization rate. Three sizing compositions were prepared from the constituents disclosed in Example 1 according to the following formulations:

| Ebecryl 810 | 80.2% | | 77.2% | | 73.9% | |
|---|---|---|---|---|---|---|
| Benzyl dimethyl Ketol | 4.8% | | 7.8% | | 11.1% | |
| Methyl ethyl ketone | 15% | | 15% | | 15% | |
| ds | TC | LOI | TC | LOI | TC | LOI |
| 20 | 8 | 18 | 28 | 15 | 39 | 16 |
| 15 | 19 | 16 | 42 | 15 | 39 | 14 |
| 10 | 51 | 15 | 67 | 15 | 57 | 13 |

As a result of this experiment, it was determined that:
The smaller the amount of photoinitiator introduced into the finish, the more the polymerization rate varies with regard to the drawing speed; and
The polymerization rate is only minimally affected when the amount of photoinitiator added to the system is increased if the drawing speed remains low.

EXAMPLE XIII

As previously noted, the sizing composition used in the invention may contain both at least a photoinitiator and a photosensitizer. The results indicated below illustrate the effect of varying the ratio of these constituents on the polymerization rate.

Three sizing compositions were made with the same constituents as in example XI. In addition, benzophenone was added as a photosensitizer.

These formulations comprise:

| Ebecryl 810: | 80.2% | | 77.4% | | 77.2% | |
|---|---|---|---|---|---|---|
| Benzyl dimethyl ketal | 2.4% | | 3.8% | | 5.5% | |
| Benzophenone | 2.4% | | 3.8% | | 2.3% | |
| Methyl ethyl ketone | 15% | | 15% | | 15% | |
| ds | TC | LOI | TC | LOI | TC | LOI |
| 20 | 8 | 17 | 5 | 15 | 33 | 16 |
| 15 | 7 | 17 | 18 | 15 | 38 | 16 |
| 10 | 15 | 15 | 56 | 20 | 68 | 17 |

As a result of the experiment, it was determined that:
When equal amounts of photostarters are used, the sizings which contain a photosensitizer and a photoinitiator in equal proportions exhibit a lower rate of polymerization than those containing only a photoinitiator; and
this difference between the two categories of sizings disappear upon adding an amount of photoinitiator which is greater than the amount of photosensitizer.

EXAMPLE XIV

This example illustrates the effect of an inert anhydrous atmosphere on the polymerization rate of the sizing. The composition was identical with that of example VII. The glass fibers were drawn at a speed of 15 meters/second. As illustrated in FIG. 5, dry nitrogen gas was blown in the direction of the fibers upon their formation and the results obtained were as follows:

| N2 Pressure (in mbar) | LOI | TC | ultimate tensile strength (g/tex) |
|---|---|---|---|
| 0 | 17 | 55 | 80 |
| 25 | 19 | 79 | 94 |
| 30 | 19 | 72 | 96 |
| 35 | 18 | 86 | 96 |

These results clearly illustrate the effect of the nitrogen gas on the breaking strength of the yarns. For purposes of comparison, it was determined that the breaking strength of identical yarn coated with a standard oil is generally between about 60 and 70 g/tex.

EXAMPLE XV

The sizing composition utilized in this example was more complex than those disclosed previously. The experiment was carried about on an "extruded rod" ordinarily obtained by pultrusion, which is a composite material ready for immediate use.

The composition of the finish was:
Oligomers:
  53.7% epoxy acrylate (Ebecryl 600)
  7.96% urethane acrylate (Ebecryl 210)
Monomer: 17.9% hexanediol diacrylate
Photoinitiator: 7.96% benzyl dimethyl ketal
Coupling agent: 2.38% methacryl silane
Wetting agent: 0.10% diethyl polyacrylate
Solvent: 10% Methyl ethyl ketone
LOI=65%, ds=0.7 meters/second TC=100%
solubility in toluene=2%

The present invention applies to all glass composition insofar as they are capable of being transformed into continuous fibers by a mechanical drawing technique. By adjusting the composition of the sizing, the yarn thus produced can be made compatible with both thermosetting and thermoplastic resins. In addition, the process of the invention makes it possible to directly produce semi-finished products, for example, rovings of preimpregnated yarns.

Furthermore, applicants' process permits the fabrication of finished, ready for use, composite products as shown in example XV. The yarn obtained by applicant's process is therefore particularly suited to reinforce products having a base comprised of organic substances. Due to the increased strength attributable to the sizing on the surface of the glass fibers, the yarns thus produced are also useful in reinforcing products formed of inorganic materials, such as cementitious compositions.

While it is apparent that the invention herein disclosed is well calculated to fulfill the objectives stated above, it will be appreciated that numerous modifications and embodiments may be devised by those skilled in the art, and it is intended that the appended claims cover all such modifications and embodiments as fall within the true spirit and scope of the present invention.

We claim:

1. A coated glass yarn produced by:
   drawing a plurality of glass fibers formed from strands of molten glass produced by a spinneret;
   applying a sizing coating to the surface of said fibers, said coating comprising; at least an oligomer selected from among polyester acrylates, modified cellulose or starch, epoxy acrylates, silicon compounds and urethane acrylates, said oligomer further comprising chlorine as an activator element a monounsaturated or polyunsaturated monomer;
   at least a photostarter composition comprising a photoinitiator compound, a photosensitizer compound or a mixture thereof, the total amount of said photostarter compound being greater than or equal to 10% by weight of the total weight of said oligomer and said monomer;
   an organic solvent; and
   an additive composition comprising at least one of a wetting agent, an adhesion promoting agent, an antishrinking agent and a coupling agent;
   gathering said coated fibers into a yarn; and
   irradiating said coated yarn with a source of actinic radiation to polymerize and/or crosslink said sizing coating.

2. A coated glass yarn produced by:
   drawing a plurality of glass fibers formed from strands of molten glass produced by a spinneret;
   directing a flow of a dry, inert gas through said fibers so as to surround the surface thereof with said gas;
   applying at least one sizing coating to the surface of said fibers, said sizing coating comprising at least on oligomer having a molecular weight ranging between about 500 and 5,000 and selected from among polyester acrylates, silicon compounds and urethane acrylates, said oligomer further comprising chlorine as an activator element;
   an acrylic monomer;
   a photostarter composition comprising a photoinitiator compound selected from among benzoin, acetophenone, sulfonylacetophenone and their respective derivatives; a photosensitizer compound selected from among the thioxanthones, benzophenone and the benzophenone derivatives, or a mixture of said photoinitiator compound and said photosensitizer compound and said photosensitizer compound, the total amount of said photostarter compound being greater than or equal to 10% by weight of the total weight of said oligomer and said monomer;
   an organic solvent; and
   at least one additive composition selected from among diethyl polyacrylate, a methacrylic derivative, a silane compound, a chlorinated oligomer, a spiro orthoester and a bicyclo orthoester;
   wherein at least one constituent of said sizing coating may be deposited separately from the remaining constituents thereof;
   gathering said coated fibers in a yarn; and
   irradiating said coated yarn with a source of ultraviolet radiation in an oxygen-free atmosphere, wherein each of said sizing coating applications is crosslinked and/or polymerized by the application of said ultraviolet radiation and further wherein each of said sizing coating applications may utilize a different sizing coating than that previously applied to said yarn.

3. A coated glass yarn comprising a plurality of glass fibers, said fibers each having a uniform organic coating thereon which has been cured by exposing a coated yarn to actinic radiation said yarn produced by:
   drawing a plurality of glass fibers from a spinneret;
   applying a sizing coating which is capable of polymerizing and/or crosslinking, when exposed to actinic radiation, to said fibers;
   gathering said coated fibers into a yarn; and
   exposing said yarn to actinic radiation to polymerize an/or crosslink said sizing coating.

4. The coated glass yarn of claim 3 wherein more than one radiation curable coating is applied to the fibers and further wherein each coating is crosslinked and/or polymerized by the subsequent irradiation step.

5. A coated glass yarn comprising a plurality of glass fibers, said fibers each having a uniform organic coating thereon which has been cured by exposing a coated yarn to actinic radiation said yarn produced by:
   drawing a plurality of fibers from a source of an inorganic material wherein said source is heated above the melting point of said material;
   applying a sizing coating, which is capable of polymerizing and/or crosslinking when irradiated, to the surface of said fibers;
   gathering said coated fibers into a yarn; and
   irradiating said yarn to polymerize and/or crosslink said sizing coating.

6. The coated glass yarn of claim 5 wherein more than one radiation curable coating is applied to the fibers, and further wherein each coating is crosslinked and/or polymerized by the subsequent irradiation step.

7. A coated glass yarn produced by:
   drawing a plurality of glass fibers formed from strands of molten glass produced by a spinneret;
   applying a sizing coating to the surface of said fibers, said coating comprising:
   at least one oligomer selected from among polyester acrylates, modified cellulose or starch, epoxy acrylates, silicon compounds and urethane acrylates, said oligomer further comprising chlorine as an activator element;
   a monounsaturated or polyunsaturated monomer;
   at least one photostarter composition comprising a photoinitiator compound, a photosensitizer compound or a mixture thereof, the total amount of said photostarter compound being greater than or equal to 10% by weight of the total weight of said oligomer and said monomer;

an organic solvent; and an additive composition comprising at least one of a wetting agent, an adhesion promotion agent, an antishrinking agent and a coupling agent;

gathering said coated fibers into a yarn; and irradiating said coated yarn with a source of actinic radiation to polymerize and/or crosslink said sizing coating, thus obtaining a coated glass yarn.

8. The coated yarn of claim 7 wherein at least one constituent of said sizing coating is deposited separately from the remaining constituents thereof.

9. The coated yarn of claim 7 which further comprises subjecting said irradiated yarn to at least one additional coating application, each of said additional coating applications being crosslinked and/or polymerized by a subsequent irradiation step.

10. The coated yarn of claim 9 wherein said additional coating application is performed with a different sizing coating than that which was first applied to said yarn.

11. The coated yarn of claim 7 wherein said actinic radiation is in the ultraviolet range.

12. The coated yarn of claim 7 wherein the coated yarn is independently irradiated by actinic radiation of at least two different wavelengths.

13. The coated yarn of claim 7 wherein said irradiation of said coated glass yarn is carried out in an oxygen-free atmosphere.

14. The coated yarn of claim 7 which further comprises directing a flow of a dry, inert gas through said fibers as they are formed so as to surround the surface thereof with said gas in the interval between their formation and the coating thereof.

15. A coated glass yarn produced by:

drawing a plurality of glass fibers formed from strands of molten glass produced by a spinneret;

directing a flow of a dry, inert gas through said fibers so as to surround the surface thereof with said gas;

applying at least one sizing coating to the surface of said fibers; said sizing coating comprising at least one oligomer having a molecular weight ranging between about 500 and 5,000 and selected from among polyester acrylates, silicon compounds and urethane acrylates, said oligomer further comprising chlorine as an activator element, an acrylic monomer, a photostarter composition comprising a photoinitiator compound selected from among benzoin, acetophenone, sulfonylacetophenone and their respective derivatives; a photosensitizer compound selected from among the thioxanthones, benzophenone and benzophenone derivatives, or a mixture of said photoinitiator compound and said photosensitizer compound, the total amount of said photostarter compound being greater than or equal to 10% by weight of the total weight of said oligomer and said monomer;

an organic solvent; and at least one additive composition selected from among diethyl polyacrylate, a methacrylic derivative, a silane compound, a chlorinated oligomer, a spiro orthoester and a bicyclo orthoester; wherein at least one constituent of said sizing coating may be deposited separately from the remaining constituents thereof;

gathering said coated fibers in a yarn; and irradiating said coated yarn with a source of ultraviolet radiation in an oxygen-free atmosphere, wherein each of said sizing coating applications is crosslinked and/or polymerized by the application of said ultraviolet radiation and further wherein each of said sizing coating applications may utilize a different sizing coating than that previously applied to said yarn, thus obtaining a coated yarn.

* * * * *